(12) United States Patent
Nakamura

(10) Patent No.: US 8,280,645 B2
(45) Date of Patent: Oct. 2, 2012

(54) METHOD AND APPARATUS OF MEASURING PARTICULATE MATTERS

(75) Inventor: Hiroshi Nakamura, Kyoto (JP)

(73) Assignee: Horiba, Ltd. (JP)

( * ) Notice: Subject to any disclaimer, the term of this patent is extended or adjusted under 35 U.S.C. 154(b) by 799 days.

(21) Appl. No.: 12/122,167

(22) Filed: May 16, 2008

(65) Prior Publication Data
US 2009/0287424 A1  Nov. 19, 2009

(51) Int. Cl.
*G01N 31/00* (2006.01)
*F01N 3/00* (2006.01)
(52) U.S. Cl. .......................................... 702/24; 60/276
(58) Field of Classification Search .............. 702/24, 702/22–23, 26–27, 29–30, 33, 45–46, 50, 702/55, 66–67, 70–71, 79, 81, 84, 127–131, 702/137–138, 179–180, 182–183, 189–190, 702/198; 73/1.02, 1.06, 1.16, 23.2, 23.31, 73/23.33, 28.01–28.02, 28.05; 324/459, 324/464, 466, 468, 470; 60/272–276
See application file for complete search history.

(56) References Cited

FOREIGN PATENT DOCUMENTS

| JP | 05045282 A | 2/1993 |
|---|---|---|
| JP | 2004117261 A | 4/2004 |
| JP | 2005009964 A | 1/2005 |
| JP | 2005091043 A | 4/2005 |
| JP | 2005514588 A | 5/2005 |
| WO | 2004046517 A2 | 6/2004 |

OTHER PUBLICATIONS

Maricq et al., Measuring Particulate Mass Emissions with the Electrical Low Pressure Impactor, 2006, Aerosol Science and Technology, 40, pp. 85-96.*
Moosmuller et al., Time Resolved Characterization of Diesel Particulate Emissions. 1. Instruments for Particle Mass Measurements, 2001, Environ. Sci. Technol. 35, pp. 781-787.*
Wei et al., "The Development of an On-Board Instrument for On-Road Diesel Particulate Measurement," SAE paper No. 2008-36-0273, SAE International, 2008.

* cited by examiner

*Primary Examiner* — Toan M Le
(74) *Attorney, Agent, or Firm* — Brooks Kushman P.C.

(57) ABSTRACT

An apparatus for measuring particulate matters includes a particulate matters collecting part 1 that collects particulate matters contained in exhaust gas from an engine 200 by a collecting filter 41 during a predetermined period while the engine 200 is dynamically driven. A second measuring part 22 continuously measures properties indirectly indicating the mass of the particulate matters contained in the exhaust gas during the predetermined period. A correlation calculating part 82 calculates a correlation between the measurement result of the mass of the particulate matters collected by the particulate matters collecting part 1 and a time integration value of the measurement result in the second measuring part 22 during the predetermined period. A converting part 83 converts the continuous measurement data in the second measuring part 22 into a time series variation of the mass of the particulate matters based on the correlation.

5 Claims, 4 Drawing Sheets

METHOD AND APPARATUS OF MEASURING PARTICULATE MATTERS

BACKGROUND OF THE INVENTION

1. Field of the Invention

The present claimed invention relates to an apparatus of measuring particulate matters that measures the mass of particulate matters contained in exhaust gas of an engine.

2. Background Art

A filter mass method is well known as a method of measuring the mass of particulate matters as being one of emission matters from an engine. The filter mass method is a method to collect the particulate matters by arranging a collecting filter on a flow channel of exhaust gas from an engine so as to measure the mass of the particulate matters by means of a balance or the like. Since it is possible for this method to directly measure the mass of the particulate matters practically having no standard substance whose properties can be specified, certainty and accuracy of measurement can be expected. As a result, a constant volume sampler (CVS) that analyzes all amount of the exhaust gas from the engine after the exhaust gas is diluted is used on a standard basis for current emission gas test among measurement apparatuses using the filter mass method.

Meanwhile, recently there is a request for measuring a time series variation of the emitted amount of the particulate matters while the vehicle is dynamically running on a road with the view of further improvement of engine performance or environmental issues. However, since the filter mass method is, so called, a measurement method of a batch type by which only accumulated mass of the particulate matters emitted during a certain period is measured, it is not possible to learn how the mass of the particulate matters varies from moment to moment in accordance with a dynamic driving situation.

Then as an alternative for the filter mass method, a flame ionization detector (FID), an electric low pressure impactor (ELPI), a scanning mobility particle sizer (SMPS) or a diffusion charger sensor (DCS) that can continuously measure the particulate matters on a real time basis has been presented and developed. The flame ionization detector is to measure a number of carbon atoms contained in sample gas, and the electric low pressure impactor and the scanning mobility particle sizer are to count a number of particles. The diffusion charger sensor is an apparatus to electrically charge a surface of particles and to measure its electrically charged amount.

In accordance with these apparatuses, it is possible to conduct measurement also while the vehicle is running on a road. However, these apparatuses measure a number of carbon atoms, a number of particulate matters or a surface area of particulate matters and do not directly measure the mass of the particulate matters. As a result, in order to obtain the mass of the particulate matters from a measurement result, it is necessary to obtain a correlation with the measurement result by the collecting filter measurement method under the same condition and to calculate the mass of the particulate matters based on the correlation.

Then it can be conceived that a correlation between the measurement result by the filter mass method and the measurement result by the electric low pressure impactor method in each driving state of the engine is obtained in advance and then the dynamic variation of the mass of the particulate matters is calculated by applying the correlation to the measurement result by the electric low pressure impactor at a time when the vehicle is running on a road.

However, since the correlation is eventually a correlation at a time when each driving state of the engine is kept at a certain static state, it is unreasonable to apply this correlation to a dynamic state wherein the vehicle is running on a road and to extrapolate the actual dynamic variation of the mass of the particulate matters.

Background information may be found in WIPO International Publication No. WO 2004/046517 A2.

SUMMARY OF THE INVENTION

The present claimed invention is to solve all of the above problems and a main object of this invention is to continuously measure a variation of the mass of the particulate matters contained in the exhaust gas under a dynamic driving situation such as running on a road.

More specifically, a method of measuring particulate matters in accordance with this invention is characterized by including a collecting step to collect particulate matters contained in exhaust gas from an engine by the use of a collecting filter during a predetermined period while the engine is in operation, a first measuring step to measure mass of the particulate matters collected in the collecting step, a second measuring step to continuously measure properties indirectly indicating the mass of the particulate matters contained in the exhaust gas during the predetermined period, a correlation calculating step to calculate a correlation between a measurement result in the first measuring step and a time integration value of a measurement result in the second measuring step during the predetermined period, and a converting step to convert the measurement result in the second measuring step into a time series variation of the mass of the particulate matters based on the correlation.

In addition, an apparatus of measuring particulate matters is characterized by comprising a particulate matters collecting part that is arranged on a flow channel from an engine and collects particulate matters contained in flowing exhaust gas, a first measuring part that measures mass of the particulate matters collected by the particulate matters collecting part, a second measuring part that continuously measures properties indirectly indicating the mass of the particulate matters contained in the exhaust gas during a predetermined period while the particulate matters are collected by the particulate matters collecting part, a correlation calculating part that calculates a correlation between a value of a batch measurement data indicating a measurement result in the first measuring part and a time integration value of a continuous measurement data indicating a measurement result in the second measuring part during the predetermined period, and a converting part that converts the continuous measurement data into a time series variation data of the mass of the particulate matters based on the correlation.

Furthermore, a program in accordance with this invention is characterized by making a computer produce functions as a data receiving part that receives a batch measurement data obtained by collecting particulate matters contained in exhaust gas from an engine in operation by the use of a collecting filter and by measuring mass of the collected particulate matters and a continuous measurement data obtained by continuously measuring properties indirectly indicating the mass of the particulate matters contained in the exhaust gas during a predetermined period while the particulate matters are collected by the collecting filter, a correlation calculating part that calculates a correlation between an integrated value of the continuous measurement data received by the data receiving part during the predetermined period and a value of the batch measurement data, and a converting part that converts the continuous measurement data into a time series variation data of the mass of the particulate matters based on the correlation.

The exhaust gas includes the gas diluted by air or the like in addition to the gas emitted from the engine. In addition, the properties indirectly indicating the mass of the particulate matters is a surface area, a number or a particle diameter distribution of the particulate matters.

If the apparatus of measuring particulate matters is so arranged to be loaded on a vehicle that actually runs on a road and to measure the particulate matters contained in the exhaust gas while the vehicle whose engine is dynamically driven is running, the apparatus in accordance with this invention meets an original object and its effect becomes especially distinctive.

Since the particulate matters do not have any specified standard substances, it is preferable that the second measuring part can measure the properties independently from the chemical properties of the substance. As the second measuring part, it can be represented by a measuring part that calculates the measurement result by setting an electrically charged amount of the particulate matters electrically charged by the use of a charged particle diffusion method as at least one of parameters.

In order to install the apparatus of measuring particulate matters on a vehicle and to complete all of the steps inside the vehicle, it is preferable that the first measuring part combusts the particulate matters collected by the particulate matters collecting part and measures the mass of the particulate matters based on a component and an amount of the combustion gas.

With this invention of the above structure, the correlation between the continuous time series data indirectly indicating the mass of the particulate matters measured while the engine is driven and the direct measurement result of the total mass of the particulate matters emitted during the engine is driven is obtained every time the engine is driven and the continuous time series data of the mass of the particulate matters is calculated based on the correlation.

As a result, it is possible to obtain the highly reliable continuous time series data of the mass of the particulate matters unlike with a conventional case using a fixed correlation obtained under a static condition that is totally different from a dynamic condition such as driving on a road.

DETAILED DESCRIPTION OF THE PREFERRED EMBODIMENTS

One embodiment of this invention will be explained with reference to drawings.

Figure 1:
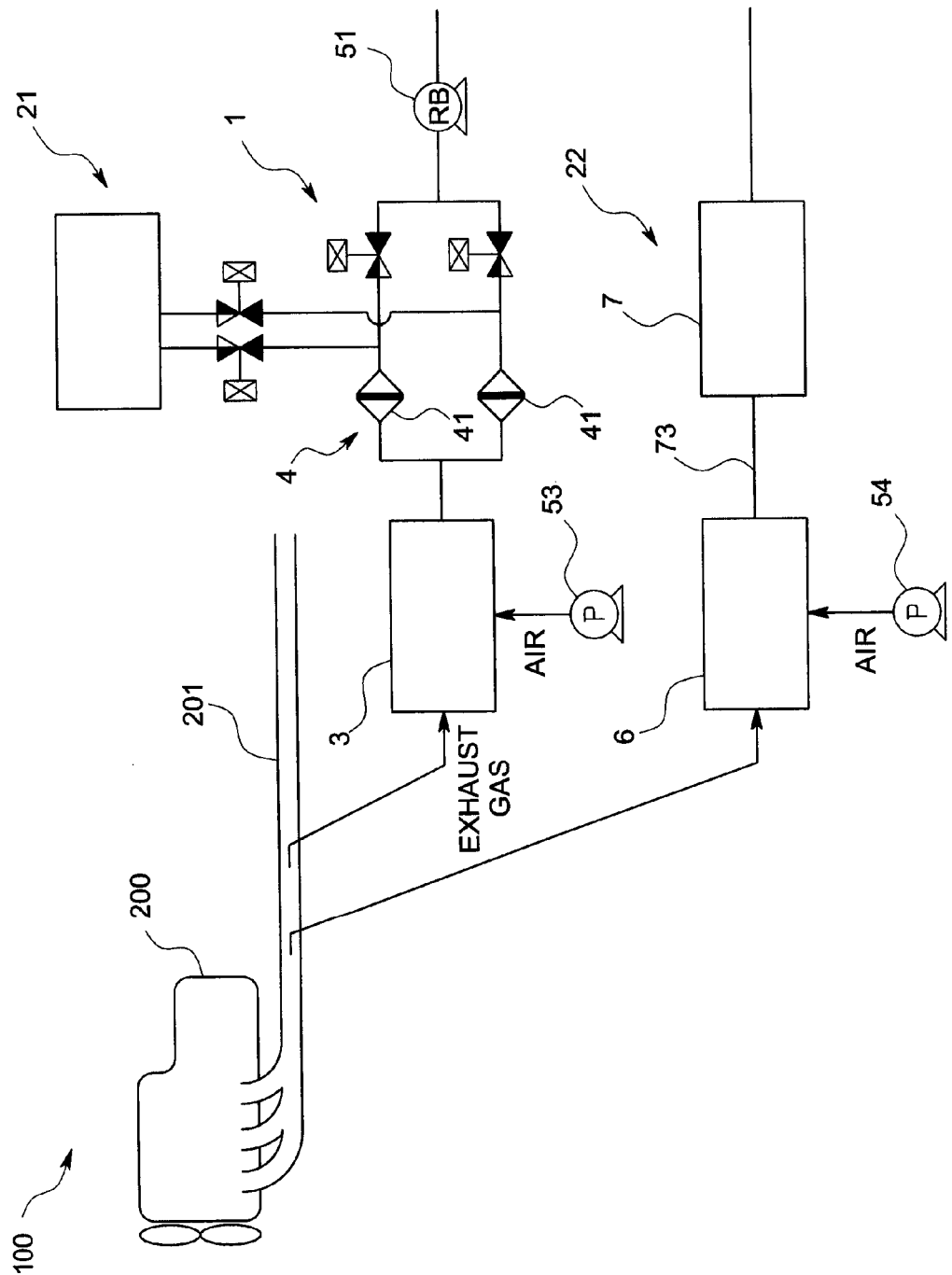
FIG. 1 is a pattern diagram of a general overall view showing an apparatus of measuring particulate matters in accordance with one embodiment of the present claimed invention.

FIG. 1 shows a whole general view of an apparatus of measuring particulate matters 100 in accordance with this embodiment. The apparatus of measuring particulate matters 100 is to measure mass concentration of the particulate matters contained in exhaust gas from an engine 200 as being an internal combustion engine, and comprises a particulate matters collecting part 1, a first measuring part 21, and a second measuring part 22, each of which is connected to an exhaust pipe 201 of the engine 200 and into each of which a part of its exhaust gas is introduced, as shown in FIG. 1.

First, the particulate matters collecting part 1 will be explained.

The particulate matters collecting part 1 is to batch-measure integrated mass of the particulate matters contained in the exhaust gas based on a filter mass method or a measurement method whose correlation with the filter mass method is obvious during a predetermined period while the engine 200 is dynamically operated, and comprises a first dilution system 3 and a collecting filter part 4.

The first dilution system 3 makes use of, for example, a micro tunnel system, introduces the exhaust gas at a certain ratio to all flow amount of the exhaust gas flowing in the exhaust pipe 201, and mixes air as being gas for dilution into the introduced exhaust gas. A flow meter, a flow control valve, and a control unit for controlling them to make an introducing amount of the exhaust gas at a certain ratio of all of the exhaust gas flow are omitted to draw in FIG. 1. The air is fed with pressure by a compressor 53 or the like. All of the exhaust gas diluted by being mixed with the air is introduced into the collecting filter part 4 through a middle pipe by the first dilution system 3.

The collecting filter part 4 has a structure wherein a collecting filter 41 is arranged on a flow channel, and collects the particulate matters contained in the diluted exhaust gas passing through the collecting filter 41. A roots blower 51 as being a suction pump is arranged downstream of the collecting filter 4.

The first measuring part 21 is to directly measure the mass of the particulate matters collected by the collecting filter 41. In order to measure the mass, the balance method may be used as is conventionally, however, this method has some problem such that a process to attach or detach the collecting filter is troublesome or the collecting filter might absorb moisture, thereby requiring a lot of time to conduct measurement. As a result, it is preferable to use, for example, a filter combustion method wherein a high correlation with a filter mass method is established. The filter combustion method is a method to calculate and measure the mass of the particulate matters based on a component and an amount of the combustion gas by heating the collecting filter 41 and burning only the collected particulate matters. The first measuring part 21 outputs a batch measurement data indicating its measurement result.

As mentioned, since the exhaust gas with a given ratio to all amount of the exhaust gas is introduced into the collecting filter 41, it is possible to calculate the mass of the particulate matters contained in all of the exhaust gas emitted during the predetermined period for collection based on the mass of the particulate matters collected by the collecting filter 41 and the above-mentioned ratio.

Next, the second measuring part 22 will be explained.

The second measuring part 22 is to continuously measure properties indirectly indicating the mass of the particulate matters contained in the exhaust gas during the predetermined period, and comprises a second dilution system 6 and a mass related properties measuring part 7.

The second dilution system 6 introduces the exhaust gas at a certain ratio to all flow amount of the exhaust gas flowing in the exhaust pipe 201 and mixes air as being gas for dilution into the introduced exhaust gas. The air is fed with pressure by a compressor 54 or the like. A flow meter, a flow control valve, and a control unit for controlling them to make an introducing amount of the exhaust gas at a certain ratio of all flow amount of the exhaust gas are omitted to draw in FIG. 1 as is the case with the first dilution system 3.

All of the exhaust gas diluted by being mixed with the air is introduced into the mass related properties measuring part 7 though a flow channel 73.

Figure 2:
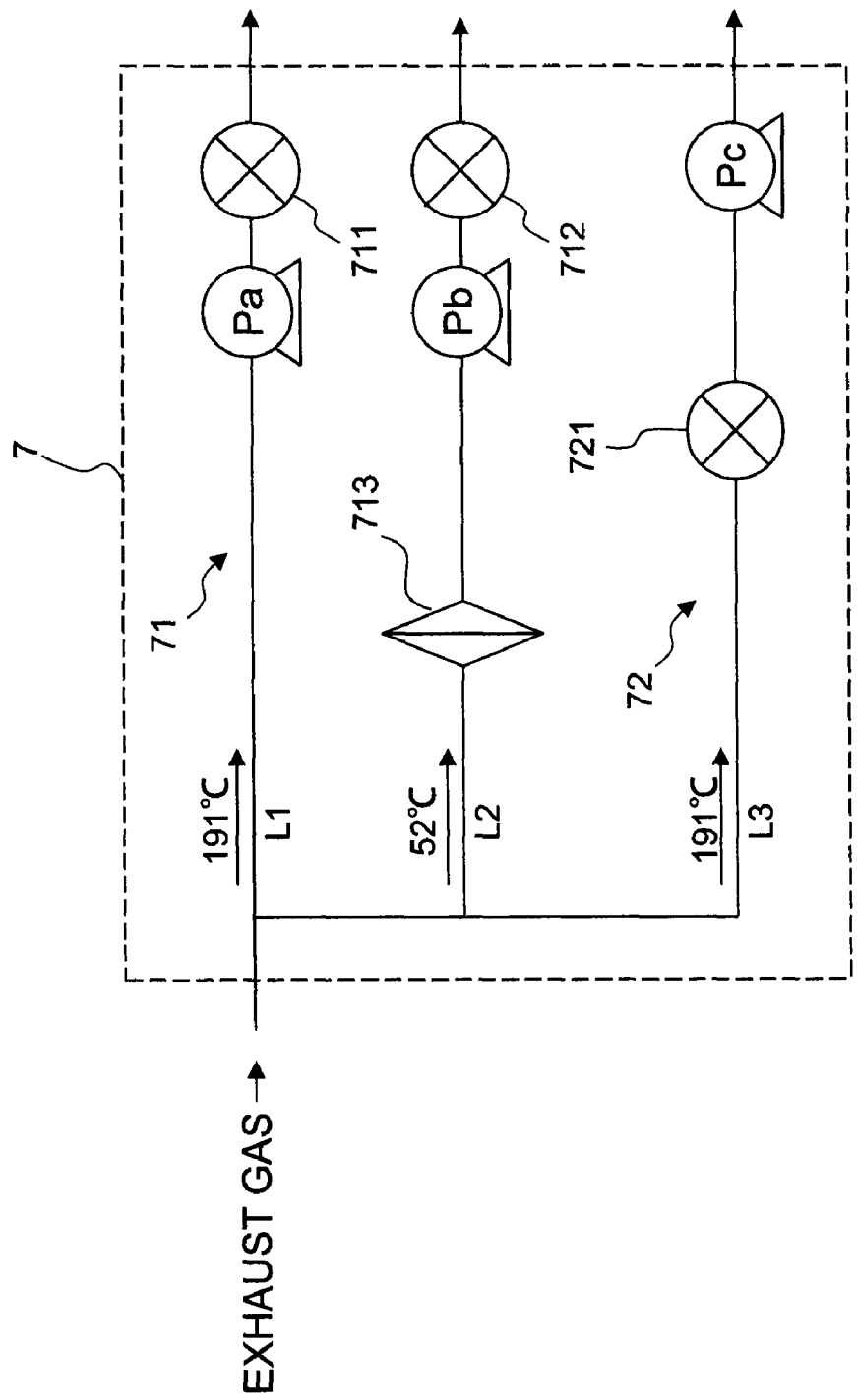
FIG. 2 is a general view showing a simplified internal structure of a mass related properties measuring part in accordance with this embodiment.

The mass related properties measuring part 7 in this embodiment, whose simplified internal structure is shown in FIG. 2, is connected in parallel to a SOF measurement system 71 and a soot measurement system 72 each of which is able to continuously measure a soluble organic fraction (SOF, mainly hydrocarbon) that is considered as a main component of the particulate matters and soot.

First, the SOF measurement system 71 will be explained.

The SOF measurement system 71 comprises, as shown in FIG. 2, a passing line L1 and a particle component removing line L2 into each of which the exhaust gas is introduced in parallel, and a sucking pump Pa and a hydrogen flame ionization detector 711 are arranged in series on the passing line L1 and a removing and collecting filter 713, a hydrogen flame ionization detector 712 and a suction pump Pb are arranged in series on the particle component removing line L2.

The passing line L1 is kept at a predetermined temperature (about 191° C.) by a temperature adjuster, not shown in drawings, and the exhaust gas flowing in the passing line L1 is directly introduced into the hydrogen flame ionization detector 711.

The particle component removing line L2 is kept at a predetermined temperature (47° C.±5° C.) by a temperature adjuster, not shown in drawings, and hydrocarbon (SOF) that liquefies or solidifies at the predetermined temperature among the particulate matters contained in the exhaust gas is removed by the removing and collecting filter 713 and the exhaust gas whose hydrocarbon is removed is introduced into the hydrogen flame ionization detector 712.

The hydrogen flame ionization detectors 711, 712 ionize hydrocarbon contained in the introduced exhaust gas, detect its ionic current and output it continuously in real time. A value of the detected signal is considered to indicate the mass (or concentration) of the SOF.

As a result, since one of the detected signals is a measurement result of the exhaust gas after the SOF is removed and the other is a measurement result of the exhaust gas containing the SOF, if difference among these values of the detected signals is obtained, it is possible to estimate and calculate the mass (or concentration) of the SOF in the particulate matters.

The soot measurement system 72 comprises a measurement line L3 into which the exhaust gas is introduced, a DC (diffusion charger) sensor 721 and a suction pump Pc both of which are arranged on the measurement line L3.

The measurement line L3 is kept at a predetermined temperature (about 191° C.) by a temperature adjuster, not shown in drawings. This is to volatilize the SOF (especially the SOF attached to soot) contained in the exhaust gas and to introduce the soot alone into the DC sensor 721.

The DC sensor 721 is to measure a surface area of the soot continuously in real time by making use of the diffusion electric charge method, and comprises an electric charge granting part that gives electric charge to the soot contained in the exhaust gas and an electric charge measuring part that measures its electric charge quantity.

The electric charge granting part, not shown in drawings, is to grant the electric charge proportional to the surface area of the soot by producing, for example, a corona discharge. The electric charge phenomenon by the corona discharge is irrelevant to chemical properties of the particle. In addition, the electric charge granting part may have another structure such that the electric charge is granted by irradiating ultraviolet rays. The electric charge measuring part, not shown in drawings, acquires the soot by the use of a grasping member such as a metal plate arranged downstream of the electric charge granting part and detects and outputs the electric current flowing at this time. A value of this detected signal represents a surface area of the soot because a quantity of the electric charge is proportional to the surface area of the soot. Since there is a predetermined relational expression between the surface area of the soot and the mass of the soot, the mass (or the concentration) of the soot can be estimated and calculated based on the value of the detected signal.

As a result, it is possible to calculate a value having some relationship with all mass of the particulate matters from a sum of a value of the detected signal in accordance with the mass of the SOF and a value of the detected signal in accordance with the mass of the soot.

The exhaust gas is separated to flow in each line L1, L2, L3 at a certain ratio by a flow amount control unit, not shown in drawings.

Furthermore, the second measuring part 22 comprises a calculating part, not shown in drawings, physically incorporated into an information processing unit to be described later or independent from an information processing unit, and calculates the mass of the SOF and the mass of the soot contained in the introduced exhaust gas based on each value of the detected signal and outputs its sum as a continuous measurement data.

Figure 3:
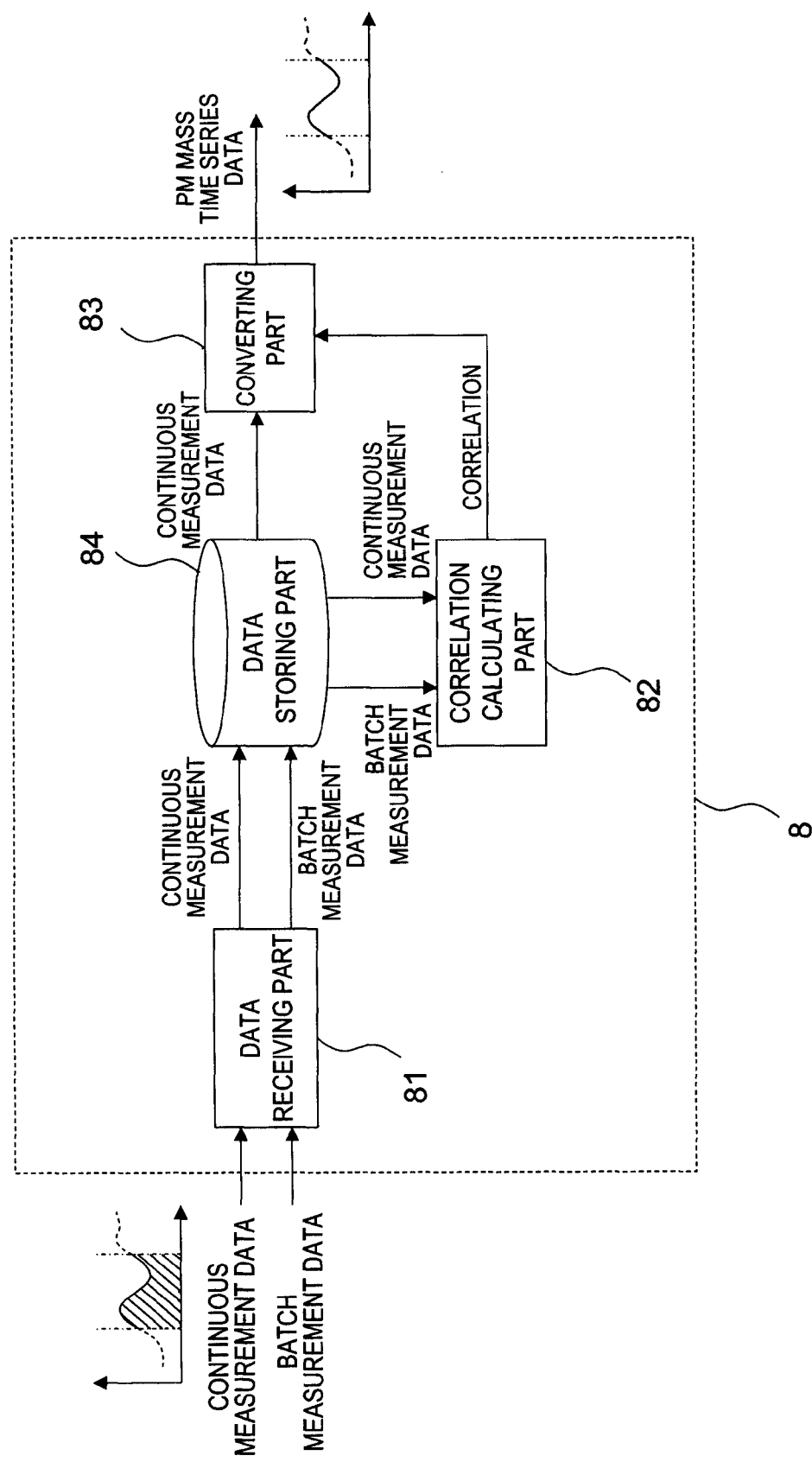
FIG. 3 is a functional block diagram showing an information processing unit in accordance with this embodiment.

In this embodiment, the information processing unit 8 as being a so-called multipurpose or dedicated computer comprising a CPU, a memory and an input/output interface is arranged. The information processing unit 8 produces functions as a data receiving part 81, a correlation calculating part 82 and a converting part 83 by operating the CPU or a peripheral device based on a predetermined program stored in the memory (refer to FIG. 3).

The data receiving part 81 receives the batch measurement data indicating an accumulated mass of the particulate matters as being the measurement result of the first measuring part 21 from the first measuring part 21 or from an input by an operator and receives the continuous measurement data output by the second measuring part 22, and then stores the batch measurement data and the continuous measurement data into a measurement result data storing part 84 set in a predetermined area of the memory.

Figure 4:
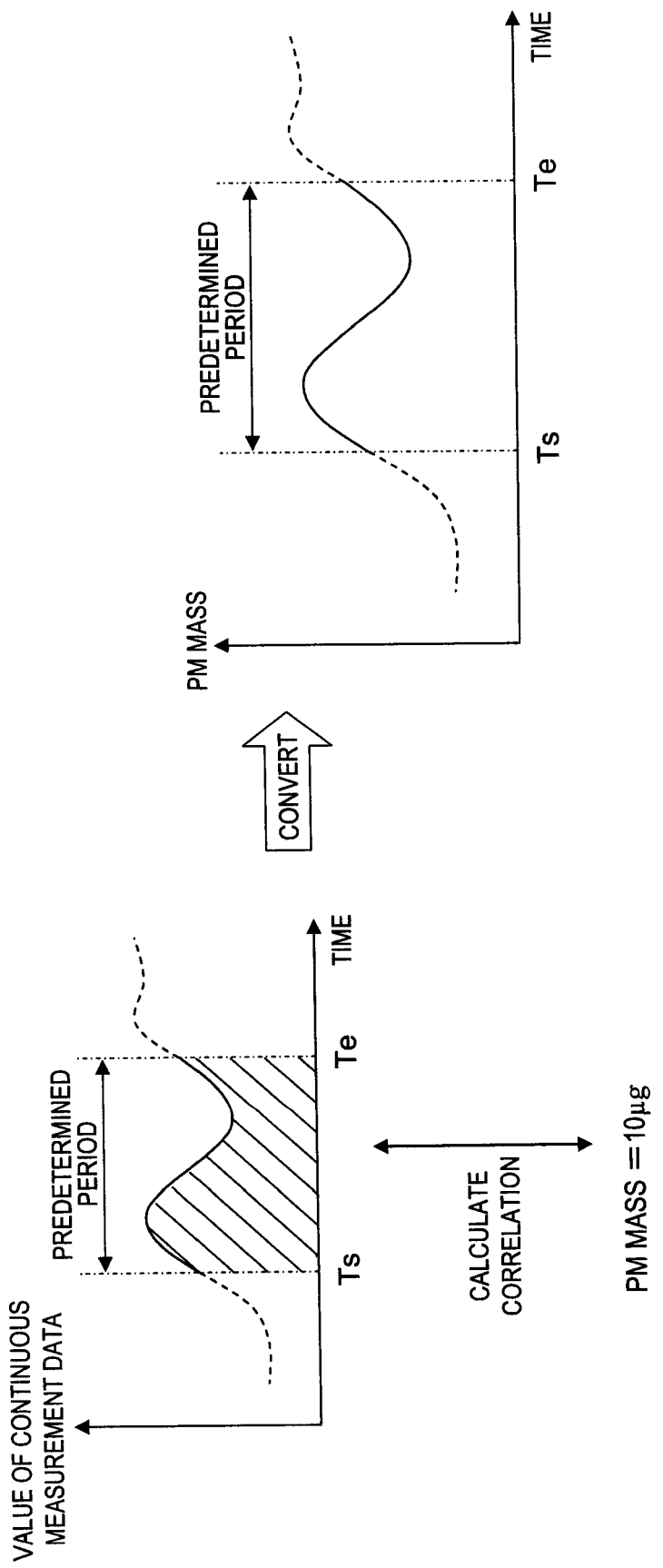
FIG. 4 is an explanatory view to help understanding of a method of measuring particulate matters in accordance with this embodiment.

The correlation calculating part 82 calculates a correlation between a value of the batch measurement data, namely the mass of the particulate matters during the predetermined period while the exhaust gas passes through the collecting filter 41 and a time integrated value of a value of the continuous measurement data during the same predetermined period (an area of a shaded portion in FIG. 4). The correlation is calculated with taking the above-mentioned dilution ratio into consideration. The correlation is a ratio between, for example, a value of the batch measurement data and a time integrated value of the continuous measurement data.

The converting part 83 converts a time series variation of the value of the continuous measurement data into a time series data of the mass of the particulate matters indicating the time series variation of the mass of the particulate matters based on the ratio (refer to FIG. 4).

The apparatus of measuring particulate matters 100 having the above-mentioned structure is loaded on a vehicle and operated in a state that the vehicle actually runs on a road. The operation of the apparatus of measuring particulate matters 100 will be explained.

First, the particulate matters contained in the exhaust gas emitted from the vehicle during the predetermined period while the vehicle is running is collected by the particulate matters collecting part 1 (collecting step). Then, the first measuring part 21 batch-measures the mass of the particulate matters collected by the collecting filter 41 by means of the balance method or the combustion method (first measuring step). The mass of the particulate matters may be measured by another measurement device arranged outside of the vehicle after the collecting filter 41 is taken out from the vehicle. The batch measurement data as being the measurement result is received by the receiving part 81 of the information processing unit 8 and stored in the measurement result accumulating part 84.

Meanwhile, the second measuring part 22 measures the exhaust gas during at least the above-mentioned predetermined period and outputs the continuous measurement data indicating its measurement result to the information processing unit 8 (second measuring step). The receiving part 81 of the information processing unit 8 stores a value of the data as the time series data into the measurement result accumulating part 84.

Next, the correlation calculating part 82 calculates a correlation between the accumulated mass value of the particulate matters shown by the batch measurement data and the time integrated value of the continuous measurement data by the second measuring part 22 during the predetermined period (correlation calculating step).

Finally, the converting part 83 converts the time series data of the continuous measurement data into the time series variation data of the mass of the particulate matters based on the correlation and outputs it to a display or the like (converting step).

Since the time series variation data of the mass of the particulate matters is calculated (or calibrated) based on the correlation with the actually measured mass of the particulate matters directly measured by the use of the filter mass method while the vehicle is running, and the correlation calculated every time the vehicle runs is used, the time series variation data of the mass of the particulate matters can be very highly reliable unlike with a conventional method using a fixed correlation obtained under a static condition that is totally different from a dynamic condition such as driving on a road.

The present claimed invention is not limited to the above-mentioned embodiment.

For example, the predetermined period to conduct measurement may be all driving period starting from a time of initiation of driving to a time of termination of driving, or may be a part of all driving period. In order to control the predetermined period, for example, an electromagnetic valve may be arranged on a pipe connected to the collecting filter 41 and the electromagnetic valve is driven to open or close by controlling the time by means of the information processing unit 8.

In addition, the second measuring part may use, for example, an electrical low pressure impactor (ELPI) or a scanning mobility particle sizer (SMPS), in addition to the above-mentioned diffusion charge sensor (DCS) or the hydrogen flame ionization detector (FID).

Each dilution system does not have any limitation in its dilution method, and may use various methods. In the above-mentioned embodiment, the dilution system of the second measuring part is different from the dilution system of the particulate matters collecting part, however, they may be communized.

In addition, it goes without saying that the present claimed invention may be variously modified without departing from a spirit of the invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of measuring particulate matters, the method comprising:
    collecting particulate matters contained in exhaust gas during a period from an engine by the use of a collecting filter while the engine is in operation;
    measuring a mass of the collected particulate matters;
    continuously measuring properties indirectly indicating the mass of the particulate matters contained in the exhaust gas during the same period of the collecting;
    calculating a ratio between the measured mass of the collected particulate matters and a time integration value of the measured properties indirectly indicating the mass of the particulate matters contained in the exhaust gas during the period of the collecting; and
    converting the measurement result from the continuous measurement of properties indirectly indicating the mass of the particulate matters into a time series variation of the mass of the particulate matters based on the ratio.

2. An apparatus for measuring particulate matters, the apparatus comprising:
    a particulate matters collecting part arranged on a flow channel from an engine for collecting particulate matters contained in flowing exhaust gas;
    a first measuring part for measuring a mass of the particulate matters collected by the particulate matters collecting part;
    a second measuring part for continuously measuring properties indirectly indicating the mass of the particulate matters contained in the exhaust gas during a same period while the particulate matters are collected by the particulate matters collecting part;
    a correlation calculating part for calculating a ratio between a value of a batch measurement data indicating a measurement result in the first measuring part and a time integration value of a continuous measurement data indicating a measurement result in the second measuring part same period; and
    a converting part for converting the continuous measurement data into a time series variation data of the mass of the particulate matters based on the ratio.

3. The apparatus for measuring particulate matters described in claim 2, wherein the apparatus is installed on a vehicle that actually runs on a road and operates to measure the particulate matters contained in the exhaust gas while the vehicle is running.

4. The apparatus for measuring particulate matters described in claim 2, wherein the second measuring part calculates the measurement result by utilizing an electrically charged amount of the particulate matters electrically charged by the use of a charged particle diffusion method as at least one of the parameters.

5. The apparatus for measuring particulate matters described in claim 2, wherein the first measuring part combusts the particulate matters collected by the particulate matters collecting part and measures the mass of the particulate matters based on a component and an amount of the combustion gas.

* * * * *